(12) United States Patent
Grote et al.

(10) Patent No.: US 6,441,236 B1
(45) Date of Patent: Aug. 27, 2002

(54) METHOD FOR PREPARING TRION-BIS (OXIME ETHER) DERIVATIVES ANDRION-MONO AND TRION-BIS(OXIME ETHER) DERIVATIVES OBTAINED THEREWITH

(75) Inventors: Thomas Grote, Schifferstadt; Bernd Wolf, Fussgönheim; Michael Rack, Heidelberg; Roland Götz, Neulussheim; Andreas Gypser, Mannheim; Adrian Steinmetz, Mannheim; Hubert Sauter, Mannheim; Michael Keil, Freinsheim; Horst Mayer, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/787,950

(22) PCT Filed: Sep. 16, 1999

(86) PCT No.: PCT/EP99/06862
§ 371 (c)(1),
(2), (4) Date: Mar. 23, 2001

(87) PCT Pub. No.: WO00/18726
PCT Pub. Date: Apr. 6, 2000

(30) Foreign Application Priority Data

Sep. 30, 1998 (DE) .......................................... 198 44 919

(51) Int. Cl.⁷ ............................................. C07C 249/00

(52) U.S. Cl. ....................................... 564/256; 564/253
(58) Field of Search ................................. 564/256, 253, 564/248, 258; 514/524, 640, 561, 562; 548/243, 370.1

(56) References Cited

U.S. PATENT DOCUMENTS 4,435,421 A    3/1984   D'Silva

FOREIGN PATENT DOCUMENTS

| EP | 940 388 | | 9/1999 |
|---|---|---|---|
| WO | WO 97/15552 | * | 5/1997 |
| WO | 98/16499 | | 4/1998 |

OTHER PUBLICATIONS

Abstract /p. 1 of WO 98/16499.

* cited by examiner

*Primary Examiner*—Samuel Barts
*Assistant Examiner*—Elvis O. Prize
(74) *Attorney, Agent, or Firm*—Keil & Weinkauf

(57) ABSTRACT

The present invention relates to a method for the production of trion-bis(oxime ether) derivatives of formula (I), wherein the substituents have the following meaning: $R^1$, $R^3$ represent unsubstituted, partially or totally halogenated $C_1$–$C_6$-alkyl or $C_3$–$C_6$-cycloalkyl; $R^2$, $R^4$ represent $C_1$–$C_4$-alkyl or a methyl substituted by $C_2$–$C_4$-alkenyl, $C_2$–$C_4$-alkinyl or phenyl and X represents oxygen or N—OH. The invention also relates to the intermediate products obtained with said method.

9 Claims, No Drawings

METHOD FOR PREPARING TRION-BIS (OXIME ETHER) DERIVATIVES AND RION-MONO AND TRION-BIS(OXIME ETHER) DERIVATIVES OBTAINED THEREWITH

The present invention relates to a process for preparing trione bis(oxime ether) derivatives of the formula I

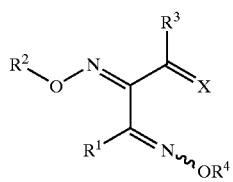

where the substituents have the following meanings:

$R^1, R^3$ are each unsubstituted, partially or fully halogenated $C_1$–$C_6$-alkyl or $C_3$–$C_6$-cycloalkyl;

$R^2, R^4$ are each unsubstituted $C_1$–$C_4$-alkyl or $C_2$–$C_4$-alkenyl-, $C_2$–$C_4$-alkynyl- or phenyl-substituted methyl and x is oxygen or N—OH.

Furthermore, the invention relates to ketals of the formula III,

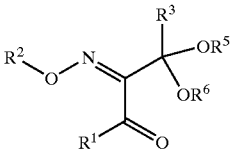

bisoxime ether ketals of the formula IV

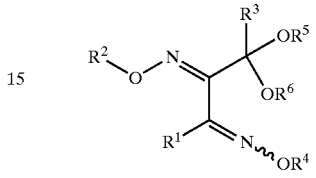

and bisoxime ether ketones of the formula Ia

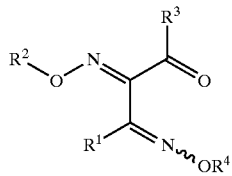

which are obtainable by this process.

Bisoxime ether ketones of the formula Ia and bisoxime ether oximes of the formula Ib are interesting intermediates for preparing the crop protection agents known from WO-A 97/15552.

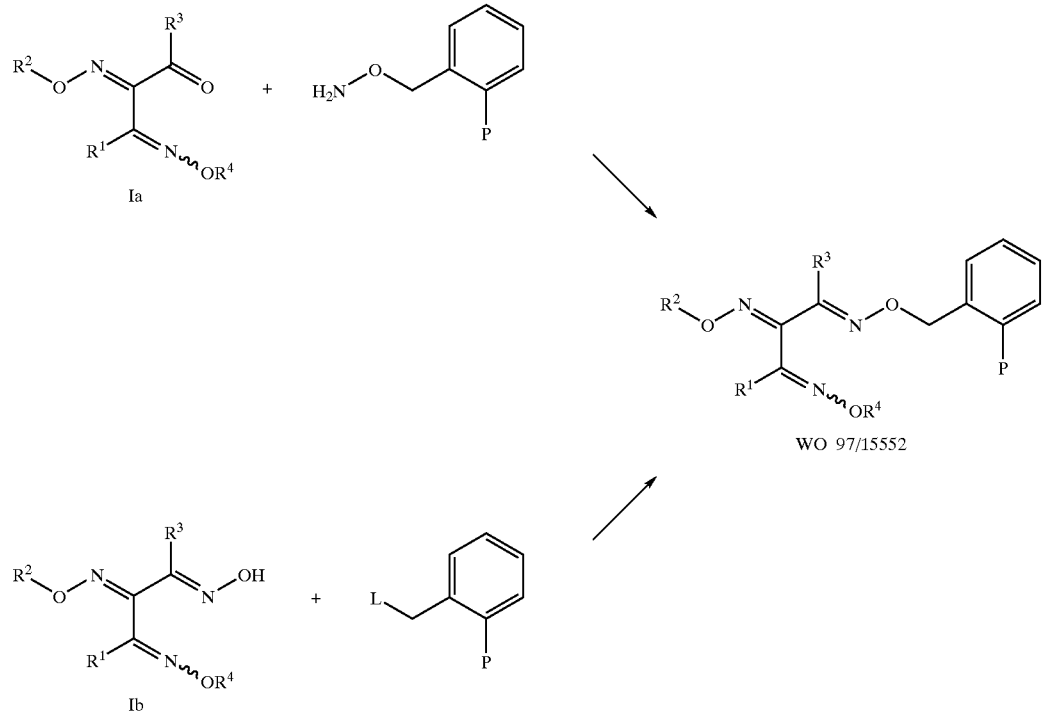

In the prior art, there are only a few documents dedicated to the synthesis of bisoxime or trisoxime derivatives of vicinal triketones. Furthermore, some of the in some cases older documents have inaccurate or erroneous structures (Gazz. Chim. Ital., 67 (1937), 388; Gazz. Chim. Ital., 52 (1922), 289). The structural elucidation of the complex mixtures of substances which are formed, for example, in the reaction of 3-(hydroxyimino)pentane-2,4-dione with hydroxylamine was only possible by modern analytical methods: in addition to the (E,E,E)- and (E,Z,E)-isomers of the pentane-2,3,4-trione trisoxime, cyclized furoxanes and isoxazoles are formed (J. Chem. Soc., Perkin Trans. II (1987), 523). Owing to the cyclic byproducts formed and the wrong regio- and stereochemistry, the substance mixtures obtained by the reaction of triketones and hydroxylamine are not suitable for synthesizing the trione bis(oxime ether) derivatives Ia and Ib.

A targeted synthesis of the bisoxime ether oximes Ib is described in WO 97/15552.

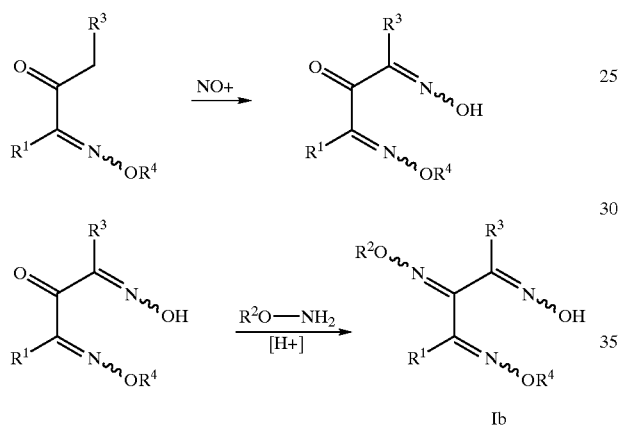

This synthesis sequence has the disadvantage that the central oxime ether function ($R^2O$—N=C) is only synthesized in the last step. Since the steric demand of the two substituents at the central carbon atom ($R^1$—C=$NOR^4$ and $R^3$—C=NOH) differs only slightly, the oximation does not proceed in a stereoselective manner and, with regard to the bond $R^2O$—N, mixtures of isomers are formed which are difficult to separate.

It is an object of the present invention to provide a process which allows the synthesis of compounds of the formulae Ia and Ib in a targeted manner and which additionally affords the desired isomers of these compounds directly, i.e. without an isomer separation.

We have found that this object is achieved by the process mentioned at the outset, which comprises
1) reacting a dione of the formula II,

where the substituents $R^1$, $R^2$ and $R^3$ are each as defined above with an alcohol or diol in the presence of an acid to give the ketal of the formula III,

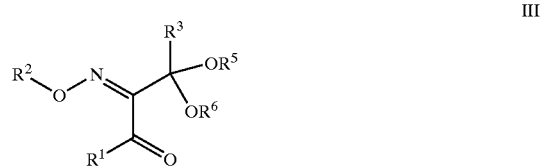

where the substituents $R^5$ and $R^6$ are each $C_1$–$C_6$-alkyl, benzyl or $C_1$–$C_3$-haloalkyl or $R^5$ and $R^6$ together with the carbon and the two oxygen atoms of the ketal function form a ring A

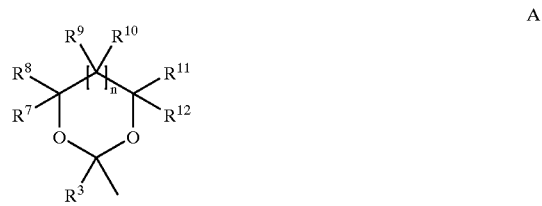

where the substituents and the index n have the following meanings:

$R^7, R^8, R^{11}, R^{12}$ are each hydrogen, halogen, $C_1$–$C_4$-alkyl, $C_1$–$C_3$-haloalkyl, $C_1$–$C_4$-alkoxymethyl, $C_2$–$C_4$-alkenyl, $C_2$–$C_4$-alkynyl or phenyl, where the latter may be substituted by nitro or halogen;

$R^9, R^{10}$ each have one of the meanings given for $R^7$, $R^8$, $R^{11}$ or $R^{12}$ and $R^9$ and $R^{10}$ together form an exo-methylene group or a carbonyl group and n is 0,1 or 2, 2) converting the result ketal III
   a) with an alkoxyamine of the formula $R^4O$—$NH_2$, where $R^4$ is as defined above, or one of its acid addition salts, or
   b) with hydroxylamine or its acid addition salt and subsequent alkylation with an alkylating agent $R^4$—$L^1$, where $R^4$ is as defined above and $L^1$ is a nucleophilically replaceable leaving group, into the bisoxime ether ketal IV,

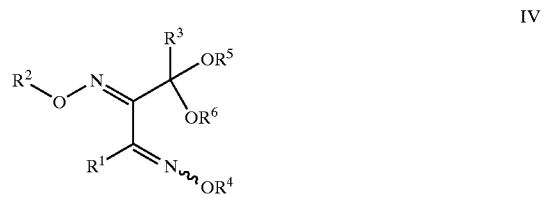

where the substituents $R^1$ to $R^6$ are each as defined above, and 3) hydrolyzing the bisoxime ether ketal IV obtained in this manner in the presence of acid, a) to give the bisoxime ether ketone Ia,

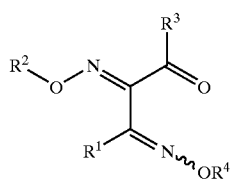

Ia or b) aminating it with hydroxylamine or its acid addition salt to give the bisoxime ether oxime Ib,

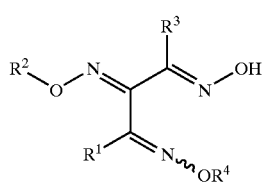

Ib

By the process according to the invention, it is possible to synthesize, in a targeted manner, compounds of the formula Ia or Ib, depending in each case on the design of step 3). A further advantage of the process is the fact that the compounds Ia and Ib are obtained in isomerically pure form with regard to the central oxime ether unit.

A particular embodiment of the process is shown in scheme 1.

By conducting the reaction in a suitable manner, it is possible to obtain preferably the E,E-isomer Ia' and E,Z,E-isomer Ib' via the bisoxime ether ketals IV' (see scheme 1):

in step 1) diols, such as, for example, ethylene glycol, 1,3-propane diol or preferably 2,2-dimethyl-1,3-propanediol are employed which afford the cyclic ketals III.

the oximation step is carried out according to variant 2a). Specifically, the ketal III is reacted with an acid addition salt of the alkoxyamine $R^4O-NH_2$ at 20–65° C. and the acid which is released during the reaction is at least partially bound by addition of bases.

in step 3a)/3b), the hydrolysis/aminolysis is started at a pH of from 0.5–1.5 and at 20–400° C.

If, on the other hand, for example dimethyl ketal IIIa ($R^5$, $R^6$=methyl), which is hydrolyzed (step 3a) or aminated (step 3b) at temperatures above 40° C., is used as starting material, the fractions of the Z-isomer Ia" or Ib" in the reaction mixture generally increase.

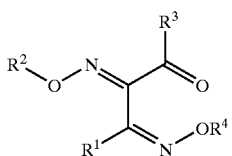

Ia"

Scheme 1

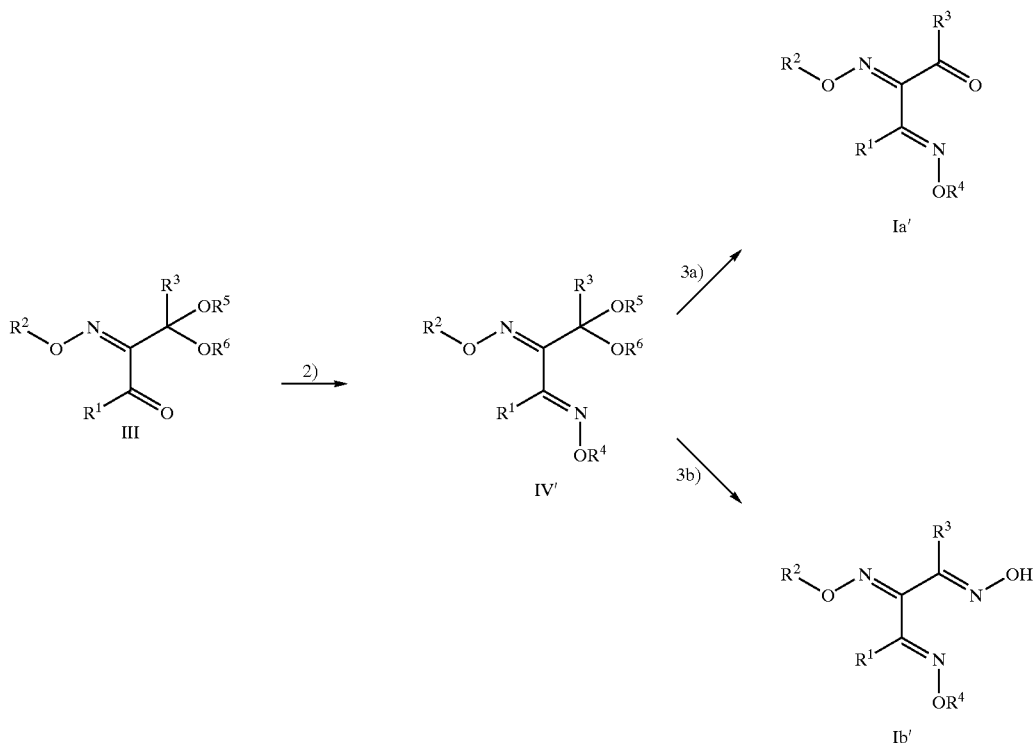

-continued

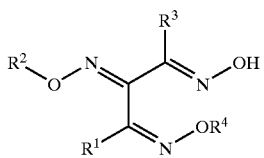

Ib''

The individual process steps are illustrated in more detail below.

1) Ketal Formation

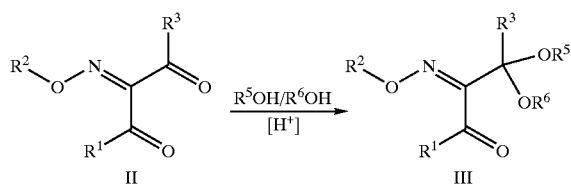

The ketal formation can generally be carried out with $C_1$–$C_6$-alkanols, such as, for example, methanol, ethanol, n-propanol, isopropanol, n-butanol, isobutanol, s-butanol, n-pentanol, with benzyl alcohol or with $C_1$–$C_3$-haloalkyl alcohols, such as, for example, 2,2,2-trichloroethanol. Particularly suitable are diols, such as, for example, o-dihydroxybenzene, ethylene glycol (1,2-ethanediol), 1-(2-nitrophenyl)-1,2-ethanediol, hex-5-ene-1,2-diol, 1,3-propanediol, 2,2-dimethyl-1,3-propanediol, 3-bromo-1,2-propanediol, 2-exo-methylene-1,3-propanediol, 2,2-dibromo-1,3-propanediol, 1,4-butanediol, 1,4-dimethoxy-2,3-butanediol. Particularly suitable are sterically demanding diols, such as 1,3-propanediol and 2,2-dimethyl-1,3-propanediol.

The ketal formation is generally carried out in the presence of acids, such as $BF_3 \times Et_2O$ (Lewis acid) or preferably Bronstedt acids, such as sulfuric acid, hydrogen chloride, hydrogen bromide or hydrogen iodide, perchloric acid, orthophosphoric acid, polyphosphoric acid, p-toluenesulfonic acid, p-dodecylbenzenesulfonic acid or camphor sulfonic acid. Preference is given to using p-toluenesulfonic acid or sulfuric acid.

The acid is usually employed in catalytic amounts of from 0.05 to 2 mol % and preferably from 0.5 to 1 mol %, based on the dione II.

The reaction temperature generally depends on the nature of the alcohol employed and is generally 20–150° C. and preferably 60–110° C. When using diols, a temperature of 60–90° C. has been found to be advantageous in many cases.

The water formed during the reaction is usually removed from the reaction mixture. To this end, the methods described in the prior art are employed (see, for example, Organikum, Barth Verlagsgesellschaft, Leipzig).

The water of reaction can, on the one hand, be removed using dehydrating agents, such as, for example, ortho esters. The ortho ester, such as, for example, trimethyl orthoformate, is generally employed in a concentration of from 1 to 1.5 molar equivalents. The reaction time is generally from 0.5 to 3 hours.

On the other hand, it has been found advantageous to remove the water of reaction using entrainers, such as toluene or cyclohexane. The end point of the reaction can be determined easily by the amount of water which is separated off. In some cases, it is advantageous to carry out the reaction at reduced pressure.

The preferred solvent is the alcohol that is required for the ketalization, which is in this case generally employed in excess. Good results were obtained using, for example, 1–10 molar equivalents of diol. If the ketalization is carried out by removal of water in the presence of an entrainer, the amount of diol can generally be reduced to 1–3 molar equivalents. Suitable solvents are furthermore hydrocarbons, such as, for example, toluene or cyclohexane, halogenated hydrocarbons, such as chlorobenzene or methylene chloride, amides, such as dimethylformamide, and ethers, such as diethyl ether or dioxane.

The reaction mixtures are worked up, for example, by extraction with a nonpolar solvent, such as an ether, halogenated hydrocarbon or, in particular, a hydrocarbon, such as cyclohexane. After the aqueous phase has been separated off, the organic phase can generally be employed directly in the subsequent oximation step. In many cases, it is not even necessary to exchange the solvent.

The diones of the formula II are known from the literature or can be prepared by methods known from the literature [cf. Indian J. Chem. B, (1991) 749–753; Bull. Acad. Sci. USSR Div. Chem. Sci. (Engl. Transl.) 28, (1979) 121–128; EP-A 416 857].

In particular, the diones II can be prepared by the procedure illustrated in more detail below.

The 1,3-diketones of the formula V

are converted by nitrozation into compounds of the formula VI,

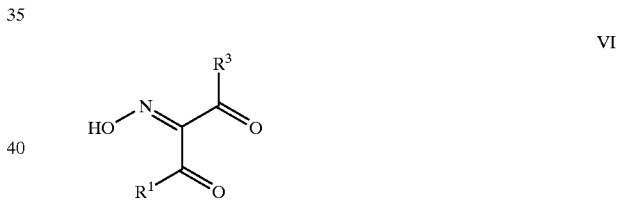

where the substituents $R^1$ and $R^3$ in the formulae V and VI are as defined in claim 1.

The nitrozation is usually carried out using sodium nitrite in the presence of a carboxylic acid or mineral acid. Acetic acid, hydrochloric acid and in particular sulfuric acid are particularly suitable.

In general, the nitrozation is carried out at from –10 to 60° C. and in particular at from 10 to 20° C.

In general, the nitrozation is carried out at a pH of from 2 to 6 and in particular at a pH of from 4 to 5.

The following process variants were found to be particularly advantageous: i) the 1,3-diketone V is initially charged in aqueous sodium nitrite solution. The acid is then added dropwise at a pH of from 4 to 5; ii) the 1,3-diketone V is initially charged in water and the acid and the aqueous sodium nitrite solution are simultaneously metered in at a pH of from 4 to 5.

Furthermore, it may be advantageous to add an organic solvent in which the compound VI is soluble, at the beginning or at the end of the reaction. The resulting solutions can be employed directly for the subsequent alkylation step. An intermediate isolation of the thermally and hydrolytically unstable compound VI can thus be avoided. In certain cases, it may furthermore be advantageous to replace the solvent used for the extraction of VI by a solvent which is more suitable for the alkylation. Solvents which are particularly suitable for the extraction are aprotic, if appropriate partially water-miscible solvents, for example halogenated hydrocarbons, such as methylene chloride, carboxylic esters, such as ethyl acetate, or ethers, such as methyl tert-butyl ether.

The alkylation of VI to the diones II can be carried out, for example, in alcohols, such as methanol, halogenated hydrocarbons, such as methylene chloride, carboxylic esters such as ethyl acetate, or ethers, such as methyl tert-butyl ether. Ketones, such as acetone, and amides, such as dimethylformamide or N-methylpyrrolidone, are particularly suitable.

Suitable alkylating agents are, for example, alkyl halides, tosylates and dialkyl sulfates. Dialkyl sulfates of the formula VII $$(R^2O)_2SO_2 \qquad \text{VII}$$

in which the substituent $R^2$ is as defined in claim 1 are particularly suitable.

The alkylation is usually carried out in the presence of bases, such as alkali metal or alkaline earth metal hydroxides, alkali metal or alkaline earth metal carbonates, alkali metal or alkaline earth metal alkoxides or tertiary amides.

The reaction temperature is generally from −20 to 100° C. and preferably from −10 to 35° C. and in particular from 0 to 25° C.

Usually, the solvent and the base are initially charged, and compound VI and the alkylating agent are then metered in simultaneously or successively.

2) Oximation

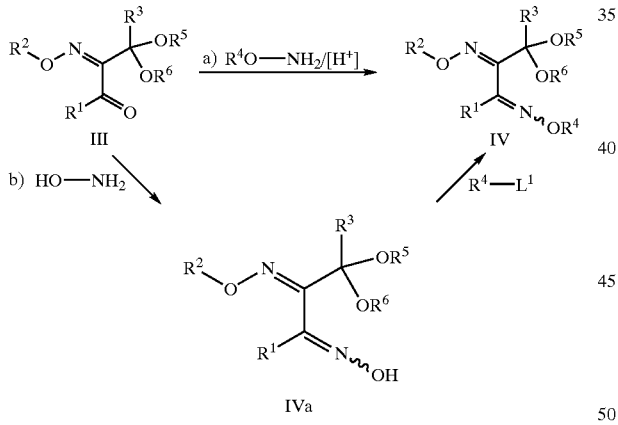

2a) The alkoxyamine $R^4O-NH_2$ is employed either in the form of an acid addition salt or as free base, where the latter can be released from the salt by addition of a strong base.

Preference is given to using the acid addition salts of the alkoxyamine. All customary acids are suitable for preparing the acid addition salts. Hereinbelow, only a few examples are given: carboxylic acids, such as acetic acid or propionic acid, dicarboxylic acids, such as oxalic acid or succinic acid, mineral acids, such as phosphoric acid or carbonic acid, and in particular hydrochloric acid or sulfuric acid.

If the acid addition salts of the alkoxyamine are employed, it is generally advantageous to add a base to bind the acid which is released during the reaction. In many cases, a pH of from 2 to 5 and in particular of from 3 to 4 has been found to be advantageous for the oximation.

In general, from 1 to 2.5 molar equivalents of a base are added. Suitable bases are, in particular, pyridines, trialkylamines, sodium hydroxide, sodium acetate and sodium methoxide. If sodium acetate is used, it is customary to add glacial acetic acid.

Conversely, it is of course also possible to employ the alkoxyamine as free base and to use one of the abovementioned acids to set the abovementioned pH range.

Suitable solvents are, for example, the solvents described in the preceding step. Also suitable are carboxylic acids, such as acetic acid, ethers, such as tetrahydrofuran, diethyl ether, methyl tert-butyl ether, or else water/pyridine mixtures. Particularly suitable are alcohols, such as methanol, ethanol, n-propanol or isopropanol.

It has furthermore been found to be advantageous to use the solvent employed in the ketalization, or the solvent mixture which is present after work-up of the ketals III, for the oximation step, too. If appropriate, it may be expedient to add other solvents to the mixture. Thus, steps 1) and 2) can be carried out as a one-pot variant.

The reaction temperature is generally from −20 to 150° C. and preferably from 0 to 100° C. and in particular from 20 to 65° C.

2b) The procedure described under 2a) can also be carried out in two steps, by firstly reacting the ketal III with hydroxylamine or its acid addition salt and subsequent alkylation with $R^4-L^1$. With regard to the way the reaction is carried out, the statements made above apply.

The reaction mixture is preferably worked up as described in the preceding step, by extractive methods.

3) Ketal Cleavage: (a) Hydrolysis and (b) Amination

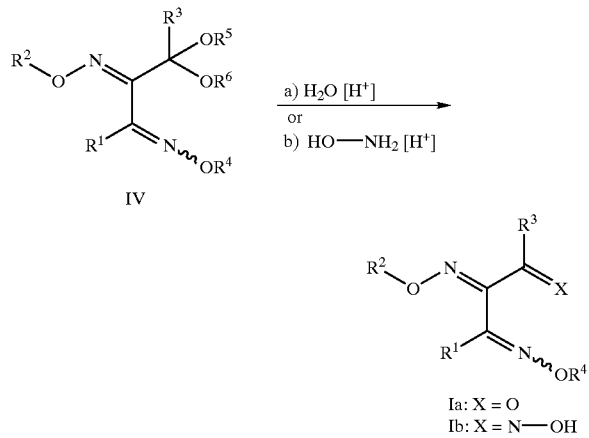

The ketal is generally cleaved in an acidic medium. A pH of from 0 to 2 and preferably from 0.5 to 1.5 has been found to be advantageous.

The pH range mentioned above can be set using any customary acid. Acetic acid, hydrochloric acid or sulfuric acid, for example, have been found to be suitable.

The cleavage of the ketal can be carried out with or without addition of a solvent. It has been found to be advantageous to use organic solvents which are stable in the abovementioned pH range (for example ethyl acetate). It may also be advantageous to use a solvent which is monophasically miscible with water/acid. Particularly suitable here are alcohols, such as, for example, methanol. The cleavage of the ketal can be carried out advantageously, for example, in water/methanol/glacial acetic acid (a suitable mixing ratio is, for example: 1/1/0.2) or ethyl acetate/water mixtures.

The aminolysis to give the compounds Ib is carried out under the conditions mentioned for the ketal cleavage, but in the presence of hydroxylamine or its acid addition salt. All customary acids are suitable for preparing the acid addition salts. Hydrochloric acid or sulfuric acid have been found to be particularly advantageous.

The hydroxylamine or its acid addition salt is generally employed in a ratio of from 1 to 2 and preferably from 1 to 1.3 molar equivalents, based on the bisoxime ether ketal IV.

The reaction temperature is generally 0–150° C. Lower reaction temperatures of from 20 to 40° C. have been found to be particularly advantageous for preparing the isomers Ia' and in particular Ib'. At high reaction temperatures (>40° C.), the proportion of the isomers Ia" and Ib" generally increases.

Work-up of the reaction mixtures is preferably carried out as described in the two preceding steps, by extraction.

The compounds of the formula Ib can be purified, for example, via their sodium salt. By adding a base, the oximes can be converted into the corresponding salt. The bisoxime ether oxime Ib can subsequently be rereleased by subsequent acidification from the salt which has been, if appropriate, separated off or purified.

The process according to the invention is particularly suitable for preparing ketals of the formula III,

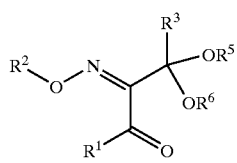

III bisoxime ether ketals of the formula IV

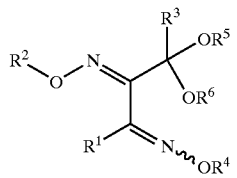

IV and bisoxime ether ketones of the formula I

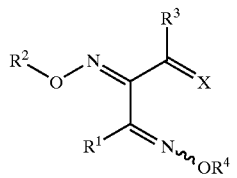

I where the substituents each have the following meanings:
$R^1, R^3$ are each unsubstituted, partially or fully halogenated $C_1$–$C_6$-alkyl or $C_3$–$C_6$-cycloalkyl;
$R^2, R^4$ are each unsubstituted $C_1$–$C_4$-alkyl or $C_2$–$C_4$-alkenyl-, $C_2$–$C_4$-alkynyl- or phenyl-substituted methyl;
X is oxygen or N—OH;
$R^5, R^6$ are each $C_1$–$C_6$-alkyl, benzyl or $C_1$–$C_3$-haloalkyl or
$R^5, R^6$ together with the carbon and the two oxygen atoms of the ketal function form a ring A,

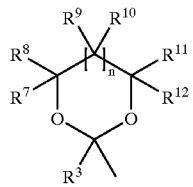

A where the substituents and the index n have the following meanings:
$R^7, R^8, R^{11}, R^{12}$ are each hydrogen, halogen, $C_1$–$C_4$-alkyl, $C_1$–$C_3$-haloalkyl, $C_1$–$C_4$-alkoxymethyl, $C_2$–$C_4$-alkenyl, $C_2$–$C_4$-alkynyl or phenyl, where the latter may be substituted by nitro or halogen;
$R^9, R^{10}$ each have one of the meanings given for $R^7$, $R^8$, $R^{11}$ or $R^{12}$ and $R^9$ and $R^{10}$ together form an exo-methylene group or a carbonyl group and
n is 0,1 or 2.

Suitable intermediates for preparing the compounds IV (where $R^4$ is not hydrogen) may be compounds of the formula IV in which $R^4$ is hydrogen (cf. formula Iva).

In the definitions of the compounds I, II and IV given above, collective terms which represent individual enumerations of each of the group members were used for the radicals $R^1$ to $R^{12}$. The radicals alkyl, alkenyl or alkynyl can be straight-chain or branched.

The term "partially or fully halogenated" is intended to express that in the groups thus characterized some or all of the hydrogen atoms may be replaced by identical or different halogen atoms.

The term "halogen" represents in each case fluorine, chlorine, bromine or iodine.

Examples of other meanings are:
$C_1$–$C_4$-alkyl:
  methyl, ethyl, propyl, 1-methylethyl, butyl, 1-methylpropyl, 2-methylpropyl and 1,1-dimethylethyl;
$C_1$–$C_6$-alkyl:
  $C_1$–$C_4$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;
$C_1$–$C_3$-haloalkyl:
  a $C_1$–$C_3$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3- pentafluoropropyl, heptafluoropropyl, 1-(fluoromethyl)-2-fluoroethyl, 1-(chloromethyl)-2-chloroethyl, 1-(bromomethyl)-2-bromoethyl;

$C_1$–$C_4$-alkoxy in the alkoxy moiety of $C_1$–$C_4$-alkoxymethyl:
methoxy, ethoxy, propoxy, 1-methylethoxy, butoxy, 1-methylpropoxy, 2-methylpropoxy and 1,1-dimethylethoxy;

$C_2$–$C_4$-alkenyl: ethenyl, prop-1-ene-1-yl, prop-2-ene-1-yl, 1-methylethenyl, but-1-ene-1-yl, but-2-ene-1-yl, but-3-ene-1-yl, 1-methyl-prop-1-ene-1-yl, 2-methyl-prop-1-ene-1-yl, 1-methyl-prop-2-ene-1-yl and 2-methyl-prop-2-ene-1-yl;

$C_2$–$C_4$-alkynyl: ethinyl, 1-propinyl, 2-propinyl, 1-butinyl, 2-butinyl, 3-butinyl, 1-methyl-2-propinyl;

$C_3$–$C_6$-cycloalkyl: cyclopropyl, cyclobutyl, cyclopentyl, cyclohexyl.

With a view to their suitability as intermediates for preparing the crop protection agents known from WO-A 97/15552, particular preference is given to the compounds of the formulae I, III and IV having the following substituents, the preference existing in each case alone or in combination:

$R^1$, $R^3$ are each methyl, ethyl, trifluoromethyl or trichloromethyl and in particular methyl or ethyl;

$R^2$, $R^4$ are each methyl, ethyl, benzyl or propargyl and in particular methyl;

X is oxygen or N—OH;

$R^5$, $R^6$ are each methyl, ethyl, n-propyl, isopropyl, n-butyl, isobutyl, s-butyl or benzyl and in particular $R^5$, $R^6$ together with the carbon and the two oxygen atoms of the ketal function form a ring A

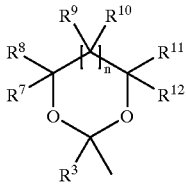

where the substituents and the index n have the following meanings:
$R^7$, $R^8$, $R^{11}$, $R^{12}$ are each hydrogen, bromine or methyl and preferably hydrogen or methyl;
$R^9$, $R^{10}$ each have one of the meanings given for $R^7$, $R^8$, $R^{11}$ or $R^{12}$ and
n is 0 or 1 and in particular 1.

With a view to their suitability as intermediates for preparing the crop protection agents known from WO-A 97/15552, preference is furthermore given to the compounds of the formulae IV', Ia' and Ib'.

Particular preference is given to the compounds listed in the reparation examples below.

PREPARATION EXAMPLES

Preparation of the Diones II (Precursors)

Pentane-2,3,4-trione 3-oxime

Variant a): In a stirred vessel, 21 l of 20% strength sulfuric acid and 6 kg (60 mol) of acetylacetone were initially charged. The mixture was cooled to about 17° C. and, at 15–20° C., 4.2 kg (60.84 mol) of 40.5% strength aqueous sodium nitrite solution were metered in. The mixture was subsequently stirred at about 17° C. for another 20 minutes and then extracted with 25 l of ethyl acetate. The organic phase was concentrated under reduced pressure, giving 7.42 kg (96% yield) of the title compound.

Variant b): 1225 g of 20% strength sulfuric acid were metered into a solution of 500 g (5 mol) of acetylacetone, 1 l of water and 1305 g of 25% strength aqueous sodium nitrite solution, the pH being adjusted to 3–5 and the internal temperature to 25–17° C. The product of value was isolated as in variant a). This gave 570 g of the title compound (89% yield).

Variant c): In parallel, 490 g (2.5 mol) of 50% strength sulfuric acid and 852 g (5 mol) of 40.5% strength strength aqueous sodium nitrite solution were metered into a mixture of 500 g (5 mol) of acetylacetone and 2 l of water, the pH being adjusted to 3.7–4.2 and the temperature to 15–18° C. Work-up as in variant a) gave 588 g of the title compound (91% yield).

Pentane-2,3,4-trione 3-(O-methyloxime)

In a 20 l vessel, 4.5 kg (32.6 mol) of potassium carbonate were suspended in 3.2 l of methyl tert-butyl ether and a liter of DMF. With stirring, the mixture was cooled to from 0 to −10° C. A solution of 4128 g (32 mol) of pentane-2,3,4-trione 3-oxime, 2 l of DMF and 4032 g (32 mol) of dimethyl sulfate was then metered in at an internal temperature of <25° C. over a period of 2 hours. The mixture was stirred at room temperature for another 3.5 hours. A further 20 l of water were then added, the upper, organic phase was removed, the aqueous phase was washed with 2 l of methyl tert-butyl ether, the combined organic phases were washed with 1 l of 5% strength hydrochloric acid and the solvent was distilled off. This gave 4214 g of the title compound in a purity of 96.6% (GC area percent), corresponding to a yield of 89%.

Preparation of the Ketals III (Step 1)

Example 1

4,4-dimethoxypentane-2,3-dione 3(E)-(O-methyloxime) (Tab.1, III.1)

4.3 g (0.03 mol) of pentane-2,3,4-trione 3-(O-methyloxime) and 6.2 g (0.06 mol) of trimethyl orthoformate were dissolved in 15 ml of methanol and admixed with a spatula tip of p-toluenesulfonic acid. The mixture was subsequently stirred at 50° C. for 5 h, after which the solvent was distilled off. This gave 5.5 g of an oil (98% yield) (phys. data see Tab. 1).

Example 2

1-(2-methyl-[1,3]dioxolan-2-yl)propane-1,2-dione 1 (E)-(O-methyloxime) (Tab.1, III.2)

2400 g (39 mol) of ethylene glycol, 430 g (3.62 mol) of trimethyl orthoformate, 550 g (3.9 mol) of pentane-2,3,4-trione 3-(O-methyloxime) and 9 g of p-toluene sulfonic acid (46 mmol) were heated with stirring to 85° C. over a period of 15 min. After 30 min at 85° C., the mixture was cooled to room temperature. During the reaction, volatile components were distilled off via a column head. For work-up, the mixture was washed with saturated sodium bicarbonate solution and extracted with methyl tert-butyl ether, and the combined organic phases were washed twice with water and finally dried over magnesium sulfate. Distillative removal of the solvent gave 580 g of a red-brown oil (phys. data see Tab. 1).

Example 3

1-(2-methyl-[1,3]dioxan-2-yl)-propane-1,2-dione 1 (E)-(O-methyloxime) (Tab.1, III.3)

Starting from 103 g (0.72 mol) of pentane-2,3,4-trione 3-(O-methyloxime), 275 g (3.62 mol) of 1,3-propanediol, 80 g (0.76 mol) of trimethyl orthoformate and 1.6 g of p-toluenesulfonic acid (9 mmol) and using the procedure of Example 2, 137 g (94% yield) of a reddish oil were obtained which, according to HPLC, had a purity of 70% (phys. data see Tab. 1).

Example 4

1-(2,5,5-trimethyl-[1,3]-dioxan-2-yl)propane-1,2-dione 1(E)-(O-methyloxime) (Tab.1, III.4)

a) Using Trimethyl Orthoformate as Dehydrating Agent

Over a period of 30 min, 430 g (3 mol) of pentane-2,3, 4-trione 3-(O-methyloxime), 1600 g (15 mol) of neopentyl glycol, 330 g (3.15 mol) of trimethyl orthoformate and 7 g of p-toluenesulfonic acid were heated with stirring to 60° C. After 90 minutes, the reaction had ended (monitored by TLC or HPLC). For work-up, the mixture was cooled to 20° C. and stirred with saturated sodium bicarbonate solution for 15 min. 1 l of water was added to the reaction mixture, which was then extracted with cyclohexane. The organic phase was washed once with water, dried over magnesium sulfate and concentrated. This gave 663 g of the title compound in a purity of 90%, which corresponds to a yield of 87% (phys. data see Tab. 1).

b) By Removal of Water (Entrainer: Cyclohexane)

100 g (0.69 mol) of pentane-2,3,4-trione 3-(O-methyloxime), 216 g (2.08 mol) of neopentyl glycol and 0.25 g of p-toluenesulfonic acid in 400 ml of cyclohexane were heated at the boil until no more water separated off in the water separator (approximately 13 hours). The reaction mixture was cooled to room temperature and admixed with water and methylene chloride. The organic phase was dried over sodium sulfate. The solvent was distilled off, giving 158.7 g of an oil of a purity of 90% according to quant. HPLC, which corresponds to a yield of 90%.

c) By Removal of Water (Entrainer: Toluene)

20 g (0.14 mol) of pentane-2,3,4-trione 3-(O-methyloxime), 43.4 g (0.42 mol) of neopentyl glycol and 0.1 g of conc. sulfuric acid in 80 ml of toluene were heated at the boil on a water separator at a pressure of 800 mbar for 2 hours. The mixture was extracted with water and toluene and then worked up as in Example 4b). This gave 30 g of an oil of a purity of 84% (yield 79%).

TABLE 1

Analytical data of selected ketals III

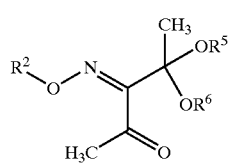

| No. | $R^5$ | $R^6$ | $R^2$ | $^1$H NMR (CDCl$_3$; δ [ppm]) |
|---|---|---|---|---|
| III.1 | Me | Me | $CH_3$ | 3.9 (s, 3 H); 3.2 (s, 6 H); 2.2 (s, 3 H); 1.4 (s, 3H) |
| III.2 | —CH$_2$CH$_2$— | | $CH_3$ | 4.0 (td, 4 H); 3.9 (s, 3 H); 2.3 (s, 3 H); 1.6 (s, 3 H) |

TABLE 1-continued

Analytical data of selected ketals III

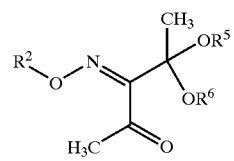

| No. | $R^5$ | $R^6$ | $R^2$ | $^1$H NMR (CDCl$_3$; δ [ppm]) |
|---|---|---|---|---|
| III.3 | —CH$_2$CH$_2$CH$_2$— | | $CH_3$ | 4.0, 3.9 (td, 4 H); 3.9 (s, 3 H); 2.3 (s, 3 H); 2.0 (bm, 1 H); 1.5 (s, 3 H); 1.5 (brd m, 1 H) |
| III.4 | —CH$_2$C(CH$_3$)$_2$CH$_2$— | | $CH_3$ | 3.9 (s, 3 H); 3.7, 3.6 (d, 4 H); 2.3 (s, 3 H); 1.5 (s, 3 H); 1.1, 0.8 (s, 3 H) |

Preparation of the Bisoxime Ether Ketals IV (Step 2)

Example 5

4,4-dimethoxypentane-2,3(E,E)-dione bis(O-methyloxime) (Tab.2, IV.1)

23 ml (0.3 mol) of pyridine and 2.5 g (0.03 mol) of methoxyamine hydrochloride were initially charged at room temperature. 5.5 g (0.03 mol) of the ketal (Example 1) dissolved in 5 ml of methanol were then added dropwise. The reaction mixture was stirred at room temperature for approximately 18 hours. For work-up, the reaction mixture was concentrated, taken up in methyl tert-butyl ether and washed successively with dist. water, dil. HCl and sodium bicarbonate solution. The mixture was dried over magnesium sulfate and the solvent was then distilled off. This gave 4 g (61% yield) of the title compound (phys. data of the E,E-isomers see Tab. 2).

Example 6

1-(2-methyl-[1,3]dioxolan-2-yl)propane-1,2-dione bis(O-methyloxime) (Tab.2, IV.2)

By the method of Example 5, 508 g (2.72 mol) of the ketal (Example 2), 430 g (5.43 mol) of pyridine and 1570 g (2.72 mol) of a 14% strength solution of methoxyamine hydrochloride in methanol gave 492 g of the title compound (phys. data of the E,E-isomers see Tab. 2).

Example 7

1-(2-methyl-[1,3]dioxan-2-yl)propane-1,2-dione bis (O-methyloxime) (Tab.2, IV.3)

a) In the Presence of Pyridine/methanol

By the method of Example 5, 50 g (0.25 mol) of the ketal (Example 3), 40 g (0.5 mol) of pyridine and 140 g (0.25 mol) of a 14% strength solution of methoxyamine hydrochloride in methanol gave 46 g of the title compound (phys. data of the E,E-isomers see Tab. 2).

b) In the Presence of Pyridine/water 45.5 g (0.2 mol) of propanediol ketal (89% pure), 125.7 g of water, 40.9 g (0.517 mol) of pyridine and 134.7 g (0.484 mol) of methoxyamine hydrochloride solution (30% strength in water) were stirred at 25° C. for 22 hours. 100 ml of methylene chloride and 300 ml of 2% strength hydrochloric acid were then added, and the organic phase was separated off. The inorganic phase was extracted twice with methylene chloride. The organic phases were combined, washed with water and subsequently dried over sodium sulfate. The solvent was distilled off. As residue, 45.1 g of the title compound having an EE-isomer content of 86.2% were obtained in a yield of 84.5%.

c) In the Presence of Sodium Acetate/methanol 239 g (0.4 mol) of 14% strength methanolic methoxyamine solution, 50 g (0.6 mol) of sodium acetate (anhydrous), dissolved in 250 ml of methanol, 75 g of magnesium sulfate and 92 g of the ketal (Example 3), dissolved in 100 ml of methanol, were initially charged at room temperature. The pH meter showed a value of 6. The mixture was stirred for 10 minutes, during which the pH decreased to 5.2, and a pH of 4.2 was set by dropwise addition of sodium acetate. The mixture was stirred at room temperature for another 20 hours and the conversion was monitored by HPLC. 7% of starting material was left. After a further 4 hours of stirring, the reaction mixture was neutralized using dilute aqueous sodium hydroxide solution and diluted with water. The mixture was extracted with methyl tert-butyl ether. The combined organic phases were washed with dilute ammonium chloride solution, dried over magnesium sulfate and concentrated. This gave 92 g (89% yield) of the title compound.

d) In the Presence of Sodium Acetate/glacial Acetic Acid/water 22.3 g (0.1 mol) of propanediol ketal (90% pure), 61 g of water, 8.2 g of sodium acetate (0.1 mol) and 55.7 g (0.2 mol) of methoxyamine hydrochloride solution (30% strength solution in water) were initially charged. A pH of 3.5 was set by addition of glacial acetic acid. The mixture was subsequently stirred at 25° C. for 4 hours, and 8.2 g (0.1 mol) of sodium acetate were then added. The mixture was stirred at 25° C. for a further 7 hours, 50 ml of methylene chloride were added and the organic phase was separated off. The aqueous phase was extracted three times with methylene chloride. The combined organic phases were washed twice with water and dried. The solvent was distilled off, and 25 g of the title compound (yield 87.8%) having an EE-isomer content of 80.8% remained.

Example 8

1-(2,5,5-trimethyl-[1,3]dioxan-2-yl)propane-1,2-dione bis(o-methyloxime) (Tab.2, IV.4)

a) Starting from Example 4

At room temperature, 350 g (4.4 mol) of pyridine and 1.3 kg (2.2 mol) of 14% strength methanolic methoxyamine hydrochloride solution were initially charged. 458 g (2.0 mol) of the ketal (Example 4) dissolved in 300 ml of methanol were added dropwise, and the reaction mixture was stirred for 18 hours. Work-up by the method of Example 5 gave 484 g (93% yield) of the title compound (phys. data of the E,E-isomers see Tab. 2).

b) Starting from pentane-2,3,4-trione 3-(O-methyloxime)

214.5 g (1.5 mol) of pentane-2,3,4-trione 3-(O-methyloxime), 2.75 g (0.0144 mol) of p-toluenesulfonic acid, 191 g (1.80 mol) of trimethyl orthoformate and 779.5 g (7.5 mol) of neopentyl glycol were heated to 85° C. over a period of approximately 15 minutes. The mixture was stirred at 85° C. for 30 minutes and subsequently cooled to 25° C. The reaction mixture was admixed with 215.8 g (2.84 mol) of pyridine and 1904 g (3.12 mol) of methoxyamine hydrochloride solution (13.7% strength in methanol) and stirred at 25° C. for 24 hours. 2803 g of water were added, the pH was set to 7 by addition of 207 ml of 50% strength aqueous sodium hydroxide solution and the mixture was extracted three times with methyl tert-butyl ether. The combined organic phases were washed twice with 5% strength hydrochloric acid and subsequently with water. The mixture was dried over sodium sulfate and the solvent was then distilled off. As residue, 334 g of the title compound having an EE-isomer content of 78.4% were obtained in a yield over two steps of 67.6%.

c) Starting from Example 10

In a stirred vessel and at 25° C., 51.5 g of ketal oxime (Example 10) and 221.5 ml of DMF were initially charged and admixed with 40.0 g (0.2 mol) of 27% strength sodium methoxide solution. The mixture was stirred at 25° C. for 30 minutes, and the methanol that had been formed was then distilled off. 27.7 g (0.22 mol) of dimethyl sulfate were then added at 20–25° C. (ice-cooling), and the mixture was stirred at 25° C. for 1 h. The reaction mixture was then concentrated using a rotary evaporator. The residue (84.8g) was taken up in 551.1 g of toluene, 33.6 g of water and 8.4 g of dimethylamine solution (40% strength) and stirred at room temperature for 1.5 h. The phases were separated and the aqueous phase was extracted with toluene. The combined organic phases were washed with water, and the solvent was then distilled off under reduced pressure. This gave 52.0 g of the title compound, corresponding to a yield of 92% (according to quantitative HPLC: 90.1% EE).

Example 9

1-(2-methyl-[1,3]dioxolan-2-yl)propane-1,2-dione 1-(O-methyloxime) 2-oxime (Tab.2, IV.5)

24 g (0.03 mol) of 50% strength aqueous sodium hydroxide solution and 200 ml of water were initially charged at 25° C. and admixed a little at a time with a total of 25 g (0.0152 mol) of hydroxylammonium sulfate. 50 g (0.0267 mol) of the ketal (Example 2) were then added dropwise, and the reaction mixture was stirred at 50° C. (pH=7–8) for 9 hours. A pH of 5–6 was then set using aqueous sodium hydroxide solution, and the mixture was stirred at 50° C. for 48 hours. Another 25 g of hydroxylammonium sulfate and 24 g of 50% strength aqueous sodium hydroxide solution were then metered in, and the mixture was stirred at 50° C. for another 20 hours. 300 ml of methyl tert-butyl ether were then added. The solid which is insoluble in the two-phase mixture was filtered off, washed with a little hexane and dried. This gave 9 g of the title compound (phys. data of the E,E-isomers see Tab. 2). The organic phase of the two-phase mixture obtained as mother liquor was dried over sodium sulfate and subsequently concentrated on a rotary evaporator. This gave another 17.5 g of the title compound.

Example 10

1-(2,5,5-trimethyl-[1,3]dioxan-2-yl)propane-1,2-dione 1-(O-methyloxime) 2-oxime (Tab.2, IV.6)

In a manner similar to that described above, 51 g of ketal (Example 4) gave 57.7 g of the title compound (purity: approximately 90%) (phys. data of the E,E-isomers see Tab. 2).

TABLE 2

Analytical data of selected bisoxime ether ketals IV $$R^2\text{-O-N}=\overset{CH_3}{\underset{}{C}}\text{-}\overset{OR^5}{\underset{OR^6}{C}}\text{-}\overset{}{\underset{H_3C}{C}}=N\text{-}OR^4$$

| No. | $R^5$ | $R^6$ | $R^2$ | $R^4$ | m.p. [°C.] | $^1$H NMR δ(ppm) |
|---|---|---|---|---|---|---|
| IV.1 | Me | Me | CH$_3$ | CH$_3$ | | CDCl$_3$: 3.9 (2s, 6 H); 3.3 (s, 3 H); 2.0 (s, 3 H); 1.6 (s, 3 H) |
| IV.2 | —CH$_2$CH$_2$— | | CH$_3$ | CH$_3$ | 60–62 | CDCl$_3$: 4.0 (td, 4 H); 3.9 (2s, 6 H); 1.9 (s, 3 H); 1.6 (s, 3 H) |
| IV.3 | —CH$_2$CH$_2$CH$_2$— | | CH$_3$ | CH$_3$ | | CDCl$_3$: 4.0 (td, 4 H); 3.9 (2s, 6 H); 2.0 (s, 3 H); 1.6 (s, 3 H) |
| IV.4 | —CH$_2$C(CH$_3$)$_2$CH$_2$— | | CH$_3$ | CH$_3$ | 45–48 | CDCl$_3$: 3.9 (2s, 6 H); 3.7, 3.4 (d, 4 H); 2.0 (s, 3 H); 1.6 (s, 3 H); 1.2, 0.8 (s, 3 H) |
| IV.5 | —CH$_2$CH$_2$— | | CH$_3$ | H | 134 | D$_6$-DMSO: 1.47 (s, 3 H); 1.82 (s, 3 H); 3.78 (s, 3 H); 3.82 (m, 2 H); 3.92 (m, 2 H); 11.18 (s, 1 H) |
| IV.6 | —CH$_2$C(CH$_3$)$_2$CH$_2$— | | CH$_3$ | H | | D$_6$-DMSO: 0.7 (s, 3 H); 1.07 (s, 3 H); 1.48 (s, 3 H); 1.9 (s, 3 H); 3.35 (d, 2 H); 3.55 (d, 2 H); 3.82 (s, 3 H); 5.2 (s, broad, OH) |

Preparation of the Bisoxime Ether Oximes Ia (Step 3a)

Example 11

Pentane-2,3,4-trione 3,4-bis(O-methyloxime)

4.2 g of Example 5 and 4.2 g of silica gel 60 were dissolved in 10 ml of acetonitrile. 10 ml of water and 3 drops of trifluoroacetic acid were added. After 30 minutes, the solid that had formed was separated off, the filtrate was extracted with cyclohexane and the solvent was distilled off. This gave 1.7 g of the title compound as an oil.

$^1$H NMR (CDCl$_3$, δ [ppm]): 3.9 (2s, 6H), 2.3 (s, 3H), 2.0 (s, 3H).

Preparation of the Bisoxime Ether Oximes Ib (Step 3b)

Example 12

Pentane-2,3,4-trione 3,4-bis(O-methyloxime) 2-oxime a) Oximation with Hydroxylammonium Chloride
aa) Starting from Example 8

387 g (1.5 mol) of Example 8, dissolved in 500 ml of methanol, were added to 125 g of hydroxylammonium chloride in 500 ml of water. 500 ml of glacial acetic acid were added, and the mixture was stirred at room temperature for 3 hours (monitored by HPLC). For work-up, the reaction mixture was neutralized with cooling with 20% strength aqueous sodium hydroxide solution. The mixture was extracted with methyl tert-butyl ether, and the solvent was removed using a rotary evaporator. The oil that remained was taken up in dil. aqueous sodium hydroxide solution and extracted with methyl tert-butyl ether. The organic phase was discarded, and the aqueous phase was acidified with HCl and extracted with methyl tert-butyl ether. The organic phase was dried over magnesium sulfate and the solvent was distilled off on a rotary evaporator.

The oil that remained crystallized on standing: 250 g (89% yield); isomer ratio: EZE/EZZ: 96:4.

$^1$H NMR (CDCl$_3$; δ [ppm]): 1.92 (s, 3H); 2.12 (s, 3H); 3.92 (s, 3H); 3.99 (s, 3H); 9.92 (s, 1H);

ab) Starting from Example 7

45 g (0.2 mol) of Example 7 (80% pure) were dissolved in 100 ml of methanol. 16 g (0.24 mol) of hydroxylammonium chloride were dissolved in 100 ml of water, and 100 ml of glacial acetic acid were added. A turbid solution formed which was stirred at room temperature for 16 hours until conversion was complete (monitored by HPLC).

For work-up, the mixture was neutralized with 50% strength aqueous sodium hydroxide solution and extracted with methyl tert-butyl ether, and the organic phase was washed with 2N NaOH. The NaOH phase was admixed with a mixture of ice and ethyl acetate, and the pH was adjusted to 2 using conc. hydrochloric acid. The mixture was extracted with ethyl acetate and the organic phase was washed with saturated sodium bicarbonate solution and water. The organic phase was dried over magnesium sulfate and concentrated, giving 29 g of an oil; isomer ratio: ZE/EZZ: 96:4.

ac) Starting from Example 6

By the method of procedure 12 aa), 216 g (1 mol) of the ketal (Example 6), and 139 g (2 mol) of hydroxylammonium chloride in a solvent mixture of 500 ml of THF, 500 ml of water and 500 ml of glacial acetic acid gave 125 g of the title compound as colorless crystals, which corresponds to a yield of 67%.

b) Oximation with Hydroxylammonium Sulfate
ba) Starting from Example 8

At 25° C., 740 ml of water, 74 ml of conc. hydrochloric acid, 148 ml of glacial acetic acid and 73.3 g (0.447 Mol) of hydroxylammonium sulfate were admixed with a solution of 297 g (0.739 Mol) of Example 8 (crude; 64.2% EE-isomer) in 740 ml of methanol. The mixture was stirred at 25° C. for 24 hours. By addition of dil. NaOH, a pH of 6 was set and the reaction solution was extracted twice with methyl tert-butyl ether. The combined organic phases were washed with saturated NaHCO$_3$ solution and dried. The solvent was distilled off on a rotary evaporator. 190.9 g of the title compound having an isomer ratio EZE:EZZ of 89.4:10.6. were isolated. According to quantitative HPLC, the yield of EZE isomer was 87.9%.

In further experiments, it was shown that the presence of the cosolvent glacial acetic acid can be dispensed with.

We claim:

1. A process for preparing trione bis(oxime ether) derivatives of the formula I

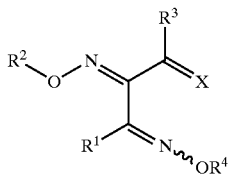

where the substituents have the following meanings:
$R^1, R^3$ are each unsubstituted, partially or fully halogenated $C_1$–$C_6$-alkyl or $C_3$–$C_6$-cycloalkyl;
$R^2, R^4$ are each unsubstituted $C_1$–$C_4$-alkyl or $C_2$–$C_4$-alkenyl-, $C_2$–$C_4$-alkynyl- or phenyl-substituted methyl and
X is oxygen or N—OH,
which comprises
1) reacting a dione of the formula II,

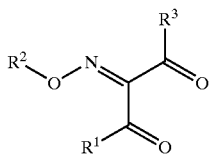

where the substituents $R^1$, $R^2$ and $R^3$ are each as defined above with an alcohol or diol in the presence of an acid to give a ketal of the formula III,

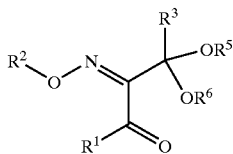

where the substituents $R^5$ and $R^6$ are each $C_1$–$C_6$-alkyl, benzyl or $C_1$–$C_3$-haloalkyl or $R^5$ and $R^6$ together with the carbon and the two oxygen atoms of the ketal function form a ring A

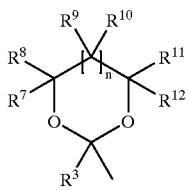

where the substituents and the index n have the following meanings:
$R^7, R^8, R^{11}, R^{12}$ are each hydrogen, halogen, $C_1$–$C_4$-alkyl, $C_1$–$C_3$-haloalkyl, $C_1$–$C_4$-alkoxymethyl, $C_2$–$C_4$-alkenyl, $C_2$–$C_4$-alkynyl or phenyl, where the latter may be substituted by nitro or halogen;
$R^9, R^{10}$ each have one of the meanings given for $R^7, R^8, R^{11}$ or $R^{12}$ and $R^9$ and $R^{10}$ together form an exo-methylene group or a carbonyl group and n is 0, 1 or 2,
2) converting the resulting ketal III
a) with an alkoxyamine of the formula $R^4O$—$NH_2$, where $R^4$ is as defined above, or one of its acid addition salts, or
b) with hydroxylamine or its acid addition salt and subsequent alkylation with an alkylating agent $R^4$—$L^1$, where $R^4$ is as defined above and $L^1$ is a nucleophilically replaceable leaving group, into the bisoxime ether ketal IV,

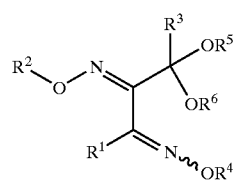

where the substituents $R^1$ to $R^6$ are each as defined above, and 3) hydrolyzing the bisoxime ether ketal IV obtained in this manner in the presence of acid,
a) to give the bisoxime ether ketone Ia,

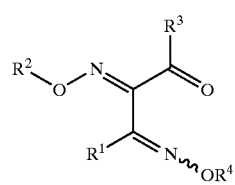

b) aminating it with hydroxylamine or its acid addition salt to give the bisoxime ether oxime Ib,

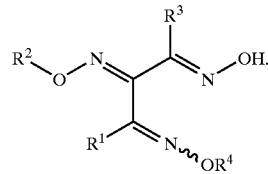

2. A process as claimed in claim 1 wherein the dione of the formula II is reacted with a diol in step 1).

3. A process as claimed in claim 2 wherein the diol employed is ethylene glycol, 1,3-propanediol or 2,2-dimethyl-1,3-propanediol.

4. A process as claimed in claim 1 wherein in step 2a) the ketal III is reacted with an acid addition salt of the alkoxyamine $R^4O$—$NH_2$ at 20–65° C. and the acid which is released during the reaction is at least partially bound by addition of bases.

5. A process as claimed in claim 1 wherein in step 3a)/3b) the hydrolysis/aminolysis is started at a pH of from 0.5 to 1.5 and is carried out at 20–40° C.

6. A ketal of the formula III,

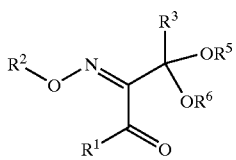

III where the substituents have the following meanings:
$R^1, R^3$ are each unsubstituted, partially or fully halogenated $C_1$–$C_6$-alkyl or $C_3$–$C_6$-cycloalkyl;
$R^2$ is unsubstituted $C_1$–$C_4$-alkyl or $C_2$–$C_4$-alkenyl-, $C_2$–$C_4$-alkynyl- or phenyl-substituted methyl;
$R^5, R^6$ are each $C_1$–$C_6$-alkyl, benzyl or $C_1$–$C_3$-haloalkyl or $R^5, R^6$ together with the carbon and the two oxygen atoms of the ketal function form a ring A,

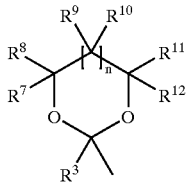

A where
$R^7, R^8, R^{11}, R^{12}$ are each hydrogen, halogen, $C_1$–$C_4$-alkyl, $C_1$–$C_3$-haloalkyl, $C_1$–$C_4$-alkoxymethyl, $C_2$–$C_4$-alkenyl, $C_2$–$C_4$-alkynyl or phenyl, where the latter may be substituted by nitro or halogen;
$R^9, R^{10}$ each have one of the meanings given for $R^7, R^8, R^{11}$ or $R^{12}$ and $R^9$ and $R^{10}$ together form an exomethylene group or a carbonyl group and
n is 0, 1 or 2.

7. A bisoxime ether ketal of the formula IV,

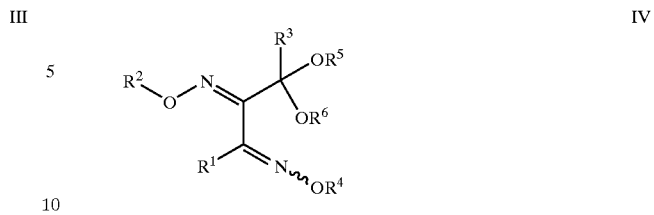

IV where $R^4$ is hydrogen, unsubstituted $C_1$–$C_4$-alkyl or $C_2$–$C_4$-alkenyl-, $C_2$–$C_4$-alkynyl- or phenyl-substituted methyl and the other substituents are each as defined in claim 6.

8. A bisoxime ether ketal of the formula IV',

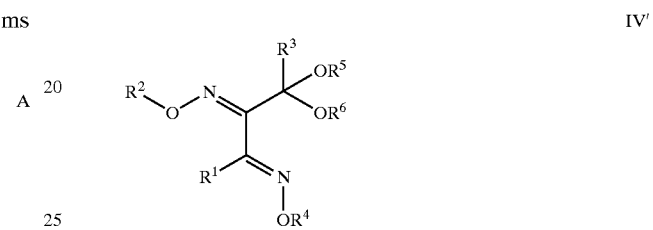

IV' where the substituents $R^1$ to $R^6$ are each as defined in claim 7.

9. A process as claimed in claim 1 wherein the diol employed is ethylene glycol and the resulting ketal is reacted with methoxyamine hydrochloride and the obtained 4,4-dimethoxypentane-2,3-dione-bis(O-methyloxime) is hydrolyzed in the presence of an acid to give pentane-2,3,4-trione-2,3-bis(O-methyloxime).

* * * * *